US00PP35072P2

(12) United States Plant Patent
Ranney et al.

(10) Patent No.: US PP35,072 P2
(45) Date of Patent: Mar. 28, 2023

(54) ***RHODODENDRON* PLANT 'NCRX9'**

(50) Latin Name: ***Rhododendron* hybrid**
Varietal Denomination: NCRX9

(71) Applicant: North Carolina State University, Raleigh, NC (US)

(72) Inventors: Thomas Green Ranney, Arden, NC (US); Darren H. Touchell, Arden, NC (US); Andra Windorf Nus, Arden, NC (US); Irene Palmer, Arden, NC (US); Nathan Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/845,475

(22) Filed: Jun. 21, 2022

(51) Int. Cl.
*A01H 5/00* (2018.01)
*A01H 6/36* (2018.01)

(52) U.S. Cl.
USPC ..... Plt./238

(58) Field of Classification Search
USPC ..... Plt./227, 238
See application file for complete search history.

*Primary Examiner* — Karen M Redden
(74) *Attorney, Agent, or Firm* — Cassandra Bright

(57) ABSTRACT

A new and distinct cultivar of *Rhododendron* plant named 'NCRX9' is disclosed, characterized by a compact habit, and pink flowers in spring that rebloom in early fall. The new cultivar is a *Rhododendron*, suitable for ornamental garden purposes.

2 Drawing Sheets

Figure 1:
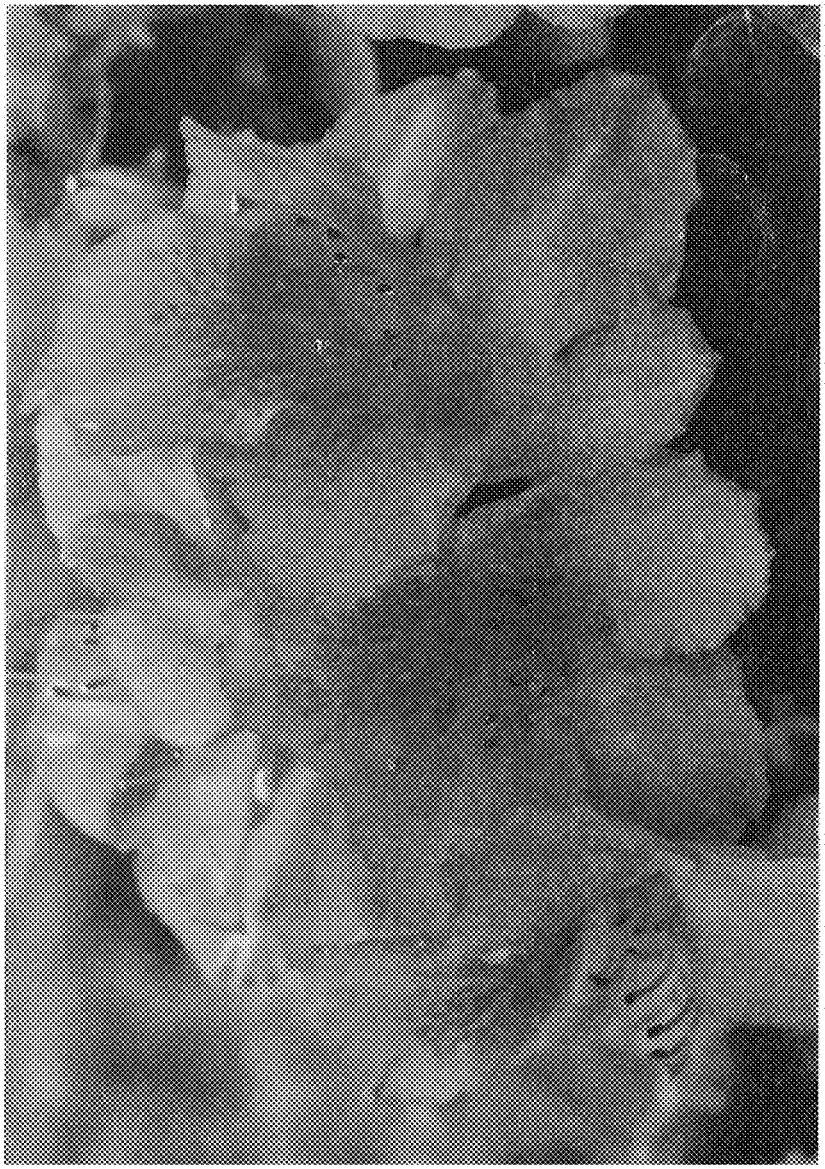

Latin name of the genus and species: *Rhododendron* hybrid.

Variety denomination: The inventive hybrid was selected from seedlings derived from a controlled cross between evergreen azaleas 'H2008-231-024' (female, unpatented experimental hybrid) and H2008-161-014 (male, unpatented experimental hybrid). Prior to the designation of the varietal denomination, 'NCRX9' was referred to by its experimental code: 'H2013-169-004'.

BACKGROUND OF THE INVENTION

The present invention comprises a new and distinct hybrid evergreen azalea cultivar hereinafter referred to by the cultivar name 'NCRX9'. This hybrid azalea was developed by a controlled breeding program at North Carolina State University, in Mills River, N.C. 'NCRX9' was selected for its large, single, bright pink flowers, floriferousness, dense and compact growth habit, and consistent reblooming. It was first selected in the Summer of 2015 from a population derived from the controlled, hand pollination of emasculated female experimental hybrid 'H2008-231-024' (unpatented) and male/pollen parent experimental hybrid 'H2008-161-014' (unpatented). The cross resulting in the new variety was conducted during the Spring of 2012.

Container trials were conducted using pine bark media supplemented with 1.04 kg·m-3 dolomitic lime, 0.74 kg·m-3 granulated micronutrients and top-dressed with 5- to 6-month slow-release fertilizer (15-9-12). Full-sun field trials were conducted in plastic-covered, bark-amended clay soils with minimum winter temperatures of −2° F. (−19° C.) and maximum summer temperatures 98° F. (37° C.).

The first asexual propagation of 'NCRX9' occurred in 2015 by rooting stem cuttings at a research nursery in Mills River, N.C. 'NCRX9' roots readily from firm softwood cuttings treated with a basal dip of 3,000 ppm indole butyric acid (potassium salt) in water. 'NCRX9' has been found to retain its distinctive characteristics through successive asexual propagations over 6 years.

SUMMARY OF THE INVENTION

The following are the unique combination of characteristics of this new cultivar when grown under standard horticultural practices at a research nursery in Mills River, N.C.

1. Floriferous spring display.
2. Large, bright pink, single flowers.
3. Dense, compact habit.
4. Consistent reblooming.

COMPARISON TO PARENT VARIETIES

'NCRX9' is similar in most horticultural characteristics to the seed parent. Plants of the new cultivar 'NCRX9' however differ in the following:

1. The new variety has large, bright pink flowers, while the seed parent has light pink flowers.
2. The new variety has a rounded, more compact habit, while the seed parent has an irregular habit.

'NCRX9' is similar in most horticultural characteristics to the pollen parent. Plants of the new cultivar 'NCRX9' however differ in the following:

1. The new variety has single flowers, while the pollen parent has semi-double flowers.
2. The new variety has a rounded, more compact habit, while the pollen parent has an irregular habit.

COMMERCIAL COMPARISON

'NCRX9' can be compared to the commercial variety *Rhododendron* 'Conlef', U.S. Plant Pat. No. 10,579. Plants of the new cultivar 'NCRX9' are similar to plants of 'Conlef' in most horticultural characteristics. Plants of the new cultivar 'NCRX9', however, differ in the following:

1. Flower color of the new variety is RHS Strong Purplish Red 60D, while the flower color of this comparator is Strong Purplish Red RHS 54A.
2. Flowers of the new variety are larger in diameter than flowers of this comparator.

BRIEF DESCRIPTION OF THE PHOTOGRAPHS

'NCRX9' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the new hybrid *Rhododendron.*

FIG. 1 is a close-up image of bright pink single flowers (RHS 60D) on 'NCRX9'. Image was taken from 3-year-old container plants grown in Grand Haven, Mich., in April 2021.

Figure 2:
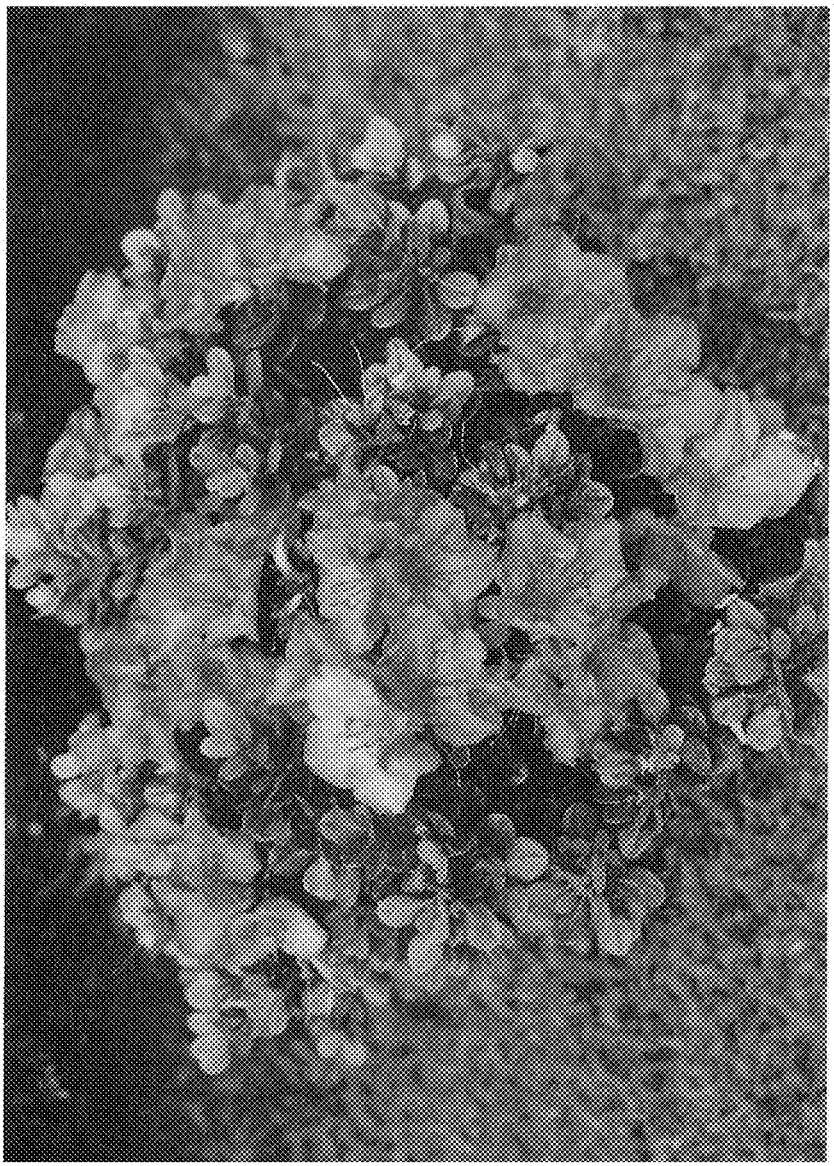

FIG. 2 Image showing floriferousness of 'NCRX9'. Image taken from 3-year-old 3-gallon container plants grown in Grand Haven, Mich., in April 2021.

DETAILED BOTANICAL DESCRIPTION

The following is a detailed description of the botanical characteristics of the new and distinct hybrid evergreen azalea known by the denomination 'NCRX9'. The detailed description was taken on a 3-year-old container-grown plant in Mills River, N.C., in 2021. Where pertinent, descriptive data was supplemented by observations/measurements taken on a 5-year-old individual located in field trials in Mills River, N.C., as well as information provided from cooperators in Grand Haven, Mich. All colors cited herein refer to The Royal Horticultural Society Colour Chart (The Royal Horticultural Society (RHS), London, 2015 Edition). Where specific dimensions, sizes, colors, and other characteristics are given, it is to be understood that such characteristics are approximations or averages set forth as accurately as is practicable.

Botanical classification: *Rhododendron* hybrid 'NCRX9'.

PROPAGATION

Typical method: Softwood cuttings.

Root description: Dense, freely branching, thin to medium texture. White to brown, not accurately measured with an RHS chart.

Time to initiate rooting: 4 to 6 weeks.

Time to produce a rooted young plant: About 3 months at 18 to 27° C.

PLANT

Plant type: Evergreen azalea.

Growth habit: Dense, rounded.

Height: 90 to 120 cm.

Width: 90 to 150 cm.

Growth rate: Moderate.

Shoots (current year's growth):

*Length.*—Average 10.1 cm (Range 8.5 to 12 cm).

*Diameter.*—Average 0.3 cm (0.2 to 0.4 cm).

*Color.*—Strong Yellow Green (RHS 144B).

*Texture.*—Densely pubescent.

Shoots (prior year's growth):

*Length.*—Average 7.6 cm (5.5 to 10 cm).

*Diameter.*—Average 0.5 cm (0.4 to 0.6 cm).

*Color.*—Dark Greyish Yellowish Brown (RHS N199B).

*Texture.*—Scurfy, sparsely pubescent.

Branches (woody branches 2-4 years old):

*Length.*—Average 8.6 cm (6 to 12 cm).

*Diameter.*—Average 0.8 cm (0.5 to 1.2 cm).

*Color.*—Moderate Yellowish Brown (RHS N199C).

*Texture.*—Glabrous.

Internode length: Average 0.6 cm (0.3 to 1 cm).

FOLIAGE

Leaf:

*Type.*—Simple, evergreen.

*Arrangement.*—Alternate.

*Shape.*—Ovate to obovate.

*Apex.*—Mucronate.

*Base.*—Cuneate.

*Margin.*—Entire, ciliate.

*Venation.*—Reticulate.

Emerging leaf:

*Color.*—Upper surface: Strong Yellow Green (RHS 144A). Lower surface: Strong Yellow Green (RHS 143C).

*Texture.*—Upper surface: Pubescent. Lower surface: Pubescent.

Mature leaf:

*Length.*—Avg. 3.0 cm (1.4 to 4.6 cm).

*Width.*—Avg. 2.0 cm (1.2 to 3.1 cm).

*Color.*—Upper surface: Greyish Olive Green (RHS NN137A). Lower surface: Moderate Yellow Green (RHS 147B).

*Texture.*—Upper surface: Pubescent. Lower surface: Pubescent.

Fall/winter leaf:

*Color.*—Upper surface: Dark Greyish Reddish Brown (RHS 200A). Lower surface: Moderate Reddish Brown (RHS 177A).

Leaf attachment: Petiolate.

Petiole:

*Length.*—Avg. 0.5 cm (0.4 to 0.7 cm).

*Diameter.*—About 0.2 cm.

*Color.*—Moderate Yellow Green (RHS 147B).

*Texture.*—Pubescent.

FLOWER

Inflorescence:

*Type.*—Congested terminal raceme (truss).

*Flowering season.*—Mid-spring (mid-April-early May into June) reblooms in early fall (late September through October).

*Flowering habit.*—Free-flowering.

*Flower number.*—2-5 flowers per truss.

*Consistency in display.*—Blooms reliably in the spring and consistently reblooms in the fall.

*Lastingness of flowers.*—Each flower lasts approximately 3-7 days.

*Fragrance.*—None.

*Self-cleaning or persistent.*—Self-cleaning.

Truss bud:

*Length.*—About 1.0 to 1.8 cm.

*Diameter.*—About 0.5 to 0.8 cm.

Bud scales:
*Number.*—4 to 7.
*Length.*—About 0.8 to 1.1 cm.
*Width.*—About 0.5 to 1.0 cm.
*Color.*—Light Yellow Green (RHS 145B).
*Texture.*—Upper side is glabrous; lower side is pubescent at tip.

Emerging flowers:
*Shape.*—Elliptic, acuminate.
*Length.*—3.0 to 4.0 cm.
*Diameter.*—1.0 to 1.5 cm.
*Color.*—Strong Purplish Red (RHS 60D).
*Texture.*—Glabrous.

Perianth:
*Shape.*—Funnel-shaped.
*Depth.*—5.0 cm (4.5 to 5.5 cm).
*Diameter at anthesis.*—7.1 cm (6.5 to 7.5 cm).
*Arrangement.*—Whorled.
*Aspect.*—Facing upwards and outwards.
*Attachment.*—Pedicellate.

Petals:
*Number.*—5.
*Length.*—5.7 cm (5.0 to 6.0 cm).
*Width.*—4.5 cm (4.0 to 5.0 cm).
*Shape.*—Obovate.
*Apex.*—Obtuse.
*Base.*—Fused.
*Margin.*—Entire, undulate.
*Color.*—Color is consistent from opening to anthesis. Upper surface: Strong Purplish Red (RHS 60D). Lower surface: Strong Purplish Red (RHS 60D). Blotch: Strong Red (RHS 53B).
*Texture.*—Glabrous.

Sepals:
*Number.*—5.
*Length.*—About 1 cm.
*Width.*—About 0.5 cm.
*Shape.*—Elliptical.
*Apex.*—Obtuse.
*Base.*—Fused.
*Margin.*—Ciliate.
*Color.*—Light Yellow Green (RHS 144D).
*Texture.*—Pubescent.

Pedicels:
*Shape.*—Rounded.
*Length.*—About 1.5 cm.
*Diameter.*—About 0.2 cm.
*Color.*—Light Yellow Green (RHS 144D) with a blush of Deep Purplish Pink (RHS 58D).
*Texture.*—Pubescent.

REPRODUCTIVE ORGANS

Gynoecium:
*Pistil number.*—1.
*Pistil length.*—About 4.5 cm.
*Stigma shape.*—Orbicular to elliptic.
*Stigma length.*—About 0.1 cm.
*Stigma width.*—About 0.2 cm.
*Stigma color.*—Moderate Purplish Red (RHS 58A).
*Style length.*—About 4 to 4.5 cm.
*Style diameter.*—About 0.1 cm.
*Style color.*—Moderate Purplish Red (RHS 58A).
*Ovary shape.*—Dome-shaped.
*Ovary length.*—0.3 to 0.5 cm.
*Ovary diameter.*—About 0.3 cm.
*Ovary color.*—Strong Yellow Green (RHS 145A).
*Texture.*—Pubescent.

Androecium:
*Stamen number.*—7-9.
*Anther shape.*—Ovoid with two apical pores.
*Anther attachment.*—Dorsifixed.
*Anther length.*—About 0.2 cm.
*Anther width.*—About 0.1 cm.
*Anther color.*—Dark Red (RHS 183A).
*Filament length.*—3.0 to 4.5 cm.
*Filament diameter.*—Less than 0.1 cm.
*Filament color.*—Moderate Purplish Red (RHS 58A).
*Amount of pollen.*—Normal.
*Pollen type.*—Thread-like.
*Pollen color.*—Yellowish White (RHS NN155D).

OTHER CHARACTERISTICS

Fruit:
*Type.*—Capsule.
*Length.*—About 0.6 to 1.0 cm if successfully pollinated, about 0.4 cm if not.
*Diameter.*—About 0.5 to 1.0 cm if successfully pollinated, about 0.4 cm if not.
*Color.*—Immature fruit color: Strong Yellow Green (RHS 145A). Mature fruit color: Moderate Brown (RHS 200D).
*Texture.*—Pubescent.

Seed:
*Number.*—0 to hundreds per capsule.
*Length.*—Approximately 0.1 cm.
*Diameter.*—Approximately 0.05 cm.
*Color.*—Moderate Orange Yellow (RHS 164B).
*Texture.*—Glabrous.

Disease and pest resistance: Not observed to be susceptible nor resistant to normal diseases and pests of *Rhododendron.*

Temperature tolerance: Has been reliably cold hardy in USDA 6B.

What is claimed is:

1. A new and distinct cultivar of *Rhododendron* plant named 'NCRX9' as herein illustrated and described.

* * * * *